(12) United States Patent
Kohno et al.

(10) Patent No.: US 6,531,320 B1
(45) Date of Patent: Mar. 11, 2003

(54) METHOD OF MONITORING REDOX OF BLOOD PLASMA USING ESR AND METHOD OF ESTIMATING PROGRESS OF DIALYSIS

(76) Inventors: Masahiro Kohno, 62-6-306, Teramachi, Hachiohji, Tokyo 193-0073 (JP); Shigeru Ohwada, 2-16-1, Sugao, Miyamae, Kawasaki, Kanagawa (JP), 216-8511

( * ) Notice: Subject to any disclaimer, the term of this patent is extended or adjusted under 35 U.S.C. 154(b) by 0 days.

(21) Appl. No.: 09/244,239

(22) Filed: Feb. 3, 1999

(30) Foreign Application Priority Data

Feb. 3, 1998 (JP) ............................................ 10-036709

(51) Int. Cl.[7] ........................ G01N 33/49; G01N 24/10; G01N 1/44
(52) U.S. Cl. .......................... 436/68; 436/35; 436/131; 436/173; 436/174
(58) Field of Search ............................ 436/35, 68, 139, 436/173, 176, 131, 174

(56) References Cited

U.S. PATENT DOCUMENTS 5,498,412 A * 3/1996 Fujie ........................ 424/195.1
5,811,305 A * 9/1998 Ono et al. ..................... 436/24

FOREIGN PATENT DOCUMENTS

JP 4-169197 * 6/1992
WO WO 92/18874 * 10/1992

OTHER PUBLICATIONS

Singh et al Annal of Rheumatic Diseases 1995;54:94–99.*
Roselaar et al Kidney International 1995; 48:199–206.*
P. Neta et al, J. Phys. Chem. 1980, 84, 532–534.*
M. Kohno et al, Bull. Chem. Soc. Japan 1991, 64, 1447–1453.*
Y. Kotake et al, J. Am. Chem. Soc. 1991, 113, 9503–9506.*
M. Minetti et al, Biochem. J. 1992, 282, 459–465.*
T. L. Greenley et al, Biochim. Biophys. Acta 1993, 1157, 23–31.*
J. W. Phillis et al, Neuroscience Lett. 1994, 169, 188–190.*
L. A. Reinke et al, Free Rad. Biol. Med. 2000, 28, 345–350.*
H. Kaneda et al, J. Food Sci. 1988, 53, 885–888.*
J. M. Burkitt et al, Free Radical Res. Commun. 1991, 14, 107–123.*
T. Ozawa et al, J. Chem. Soc., Chem. Commun. 1991, 330–332.*
J. C. Ireland et al, CHemosphere 1992, 25, 383–396.*
T. Ozawa et al, Biochem. Int. 1992, 26, 477–483.*
M. Komatsu et al, Neurosciences 1994, 20(Supplement), P133–P136.*
K. Gwozdzinski et al, Acta Biochem. Pol. 1997, 44, 99–108.*
G. S. Timmins et al, Redox Rep. 1997, 3, 125–133.*
B. Bosterling et al, Biochem. Biophys. Res, Commun. 1981, 98, 569–575, Jan. 1981.*
B. E. Britigan et al, J. Biol. Chem. 1990, 265, 2650–2656, Feb. 1990.*
K. Makino et al, Biochem. Biophys. Res. Commun. 1990, 172, 1073–1080, Nov. 1990.*
B. E. Britigan et al, Biochim. Biophys. Acta 1991, 1075, 213–222.*

(List continued on next page.)

Primary Examiner—Arlen Soderquist

(57) ABSTRACT

A method of judging the redox (oxidation-reduction) in human blood plasma precisely in a short time using electron spin resonance (ESR) spectroscopy is provided. Also, a method of evaluating the functions of human kidneys, judging whether a dialysis is necessary, determining the dialysis time and judging the usefulness of dialysis materials is offered. First, a spin-trapping agent such as PBN is added to a human blood plasma, resulting in hydroxyl radicals in the plasma. The radicals are trapped and converted into a stable spin adduct (PBN-OH). The amount of the spin adduct is measured by an ESR spectrometer.

8 Claims, 4 Drawing Sheets

OTHER PUBLICATIONS

M. Ohminato Sei Marianna Ika Diagaku Zasshi 1991, 19, 395–405.*

K. T. Yamaguchi et al, Free Radical Res. Commun. 1992, 16, 167–174, Mar. 1992.*

K. Takeuchi et al, Kassei Sanso Furi Rajikaru 1992, 3, 627–636, May 1992.*

H. Shi et al, Shengwu Wuli Xuebao 1993, 9, 483–487, Mar. 1993.*

M. Kadkhodaee et al, Free Radical Res. 1996, 25, 31–42, Jul. 1996.*

S. Nagase et al, J, Am. Soc. Nephrol. 1997, 8, 1157–1163, Jul. 1997.*

"Electron spin resonance spectroscopic demonstration of the generation of reactive oxygen species by diseased human synovial tissue following ex vivo hypoxia–reoxygenation". D. Singh et al., *Annals of the Rheumatic Diseases,* 1995; 54: 94–99.

"Detection of oxidants in uremic plasma by electron spin resonance spectroscopy", Simon E. Roselaar, et al., *Kidney International,* vol. 48 (1995), pp. 199–206.

* cited by examiner

METHOD OF MONITORING REDOX OF BLOOD PLASMA USING ESR AND METHOD OF ESTIMATING PROGRESS OF DIALYSIS

FIELD OF THE INVENTION

The present invention relates to a method of quickly and precisely monitoring the redox (oxidation-reduction) level of human blood plasma by the use of electron spin resonance (ESR) spectroscopy and to a method of estimating the progress of a dialysis according to the result of the monitoring.

DESCRIPTION OF THE PRIOR ART

Human blood plasma has homeostasis, i.e., has the ability or tendency to maintain internal equilibrium of biological functions by adjusting its physiological processes. However, where the plasma is taken out of the body, if a slight amount of oxygen is mixed into it, an oxidation reaction will progress. The details of the deterioration induced by oxidation reactions are understood only a little, due in part to the presence of anti-oxidants such as vitamins C and E. However, it is known that as oxidation reactions progress, the peroxide value of lipid in the plasma increases. It is said that the amount of peroxides is indicative of oxidation reactions. However, no report is made of the oxidation process that increases the peroxide value. It is reported that the peroxide amount in the body is varied by renal failure, which in turn varies the amount of active oxygen generated. However, no report is made of direct measurement of this variation.

It is quite important in the medical treatment of a kidney failure patient to determine if dialysis is immediately necessary or to determine the dialysis time if the dialysis is done. In the past, medical treatment was generally determined based on values obtained by various observations in judging the condition of a kidney failure patient. Hence, a quite high level of judgment technique has been required. Furthermore, any method of precisely judging the progress of a dialysis and precisely determining the end of the process has not heretofore existed. Therefore, prior art dialysis sessions have been routinely conducted for more than a sufficient time, whether the patient is in a serious or mild condition.

SUMMARY OF THE INVENTION

The present invention is intended to solve the foregoing problems, and provides a method of precisely judging the redox level of blood plasma in a short time using electron spin resonance (ESR) spectroscopy. This same method can also be used to estimate the progress of a dialysis in a short time by ESR. More particularly, the invention is a method of judging the redox of blood plasma by ESR spectroscopy such that active oxygen generated when the human blood plasma is placed in the presence of oxygen is trapped by a spin-trapping agent and that the amount of the generated spin adduct is measured by an ESR spectrometer. The progress of a dialysis is judged by electron spin resonance spectroscopy in accordance with the manner described below. First, blood plasma is taken from a dialysis patient. Active oxygen generated in the plasma under the presence of oxygen is trapped by a spin-trapping agent. The amount of the generated spin adduct is measured using an ESR spectrometer.

DETAILED DESCRIPTION OF THE INVENTION

Figure 1A:
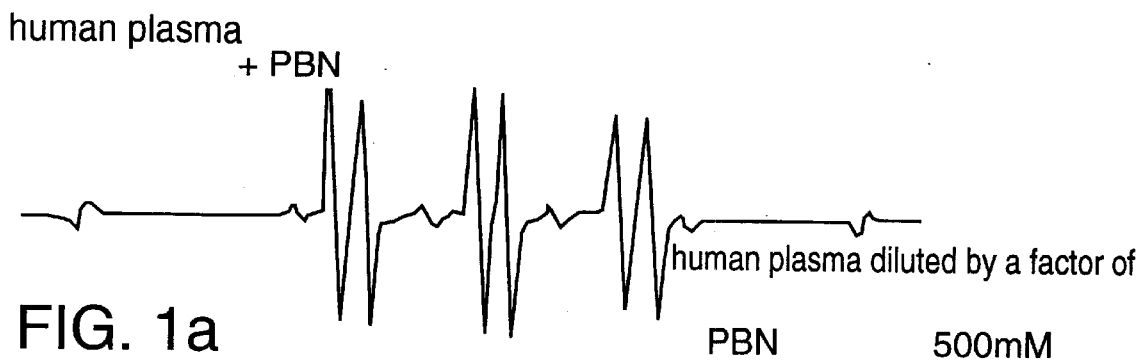
FIG. 1(a) is an ESR spectrum of a human blood plasma, obtained using PBN as a spin-trapping agent.

The present invention is intended to solve the foregoing problems, and provides a method of precisely judging the redox level of blood plasma in a short time using ESR spectroscopy. This same method can also be used to estimate the progress of a dialysis in a short time by ESR. More particularly, the invention is a method of judging the redox of blood plasma by spectroscopy such that active oxygen generated when the human blood plasma is placed in the presence of oxygen is trapped by a spin-trapping agent and that the amount of the generated spin adduct is measured by an ESR spectrometer. The progress of a dialysis is judged by electron spin resonance spectroscopy in accordance with the manner described below. First, blood plasma is taken from a dialysis patient. Active oxygen generated in the plasma under the presence of oxygen is trapped by a spin-trapping agent. The amount of the generated spin adduct is measured using an ESR spectrometer.

We have found that the redox level of a human blood plasma can be judged by investigating the behavior of the generated active oxygen which is considered to induce deterioration due to oxidation in the human blood plasma. In particular, where the human blood plasma is stored under the presence of oxygen, active oxygen is oxidatively generated and quickly disappears. We have found that diseases such as circulatory ailments, especially kidney failure, can be forecasted and judged by evaluating the ability of the blood plasma to generate active oxygen and the ability to eliminate active oxygen (the ability to resist oxidation).

Active oxygen generated in the human blood plasma has a short life and so it is difficult to measure the amount as it is. In the present invention, a spin-trapping agent is added to trap the generated active oxygen. The resulting spin adduct is stable. Therefore, the amount can be measured by an ESR spectrometer.

For example, PBN α-phenyl-N-t-butylnitrone that produces a relatively stable spin adduct on heating can be used as the spin-trapping agent. Alternative spin-trapping agents are 4-POBN (α-(4-pyridyl-1-oxide)-N-t-butylnitrone) and 4-PyBN (α-(4-pyridyl)-N-t-butylnitrone). The amount of the spin adduct can be quantified by using a stable radical such as 4-OXO-TEMPO (TEMPO is 2,2,6,6-tetramethyl-1-piperidinyloxy) radical as a reference substance. Alternative stable radicals are 4-hydroxy-TEMPO and 4-amino-TEMPO.

The human blood plasma has the ability to generate active oxygen and the ability to consume the oxygen. Overall evaluations of these abilities can be made by investigating the behavior of generated active oxygen by an ESR spectrometer. For example, they can be evaluated by storing human blood plasma under the presence of oxygen at a certain temperature (e.g., 60° C.) slightly higher than room temperature for a given time (e.g., 20 minutes) and finding the amount of spin adduct (defined as the ability to generate active oxygen). Furthermore, an evaluation can be made from the tilt of a line formed by plotting the amount of the generated active oxygen. As the tilt of the line becomes shallower, the ability to generate active oxygen becomes lower. This ability decreases as the value of anti-oxidants within the human blood increases. That is, as the ability to eliminate active oxygen is enhanced, the ability to generate active oxygen lowers. The blood plasma of a healthy person exhibits a certain level of ability to generate active oxygen. It has been confirmed that patients with kidney failure show decreased ability to generate active oxygen.

Other objects and features of the invention are apparent from the Examples, which follow.

EXAMPLE 1

Blood was taken with EDTA from kidney failure patients and from healthy persons. The blood plasma was separated and diluted by a factor of 10 with physiological saline, thus creating specimens.

Then, 300 μl of each of these specimens was taken and put into each of five test tubes. Subsequently, 100 μl of PBN (0.5-M ethanol) was put into each test tube. The test tubes were sealed and maintained at an elevated temperature of 60° C. The test tubes were taken out of the elevated-temperature environment when 0 minute, 30 minutes, 40 minutes, 60 minutes and 80 minutes passed, respectively, and put into the resonant cavity of an ESR spectrometer. Then, ESR measurements were performed.

Air existed in the space over the specimen in each test tube. Each specimen reacted with the oxygen in the air, generating active oxygen, which was trapped by the PBN. The amount of the spin adduct was measured by the ESR spectrometer. The amount was quantified with reference to the signal intensity obtained from a reference specimen of a known concentration.

The measurements were carried out using an electron spin resonance spectrometer JES-RE1X manufactured by JEOL Ltd. The magnetic field was 3350±100 Gauss. The magnetic field was modulated at 100 kHz, 1 Gauss. The microwave output was 5 mW. The amplification factor was $2 \times 10^3$. The response time was 1 second. The sweep time was 8 minutes.

Figure 1B:
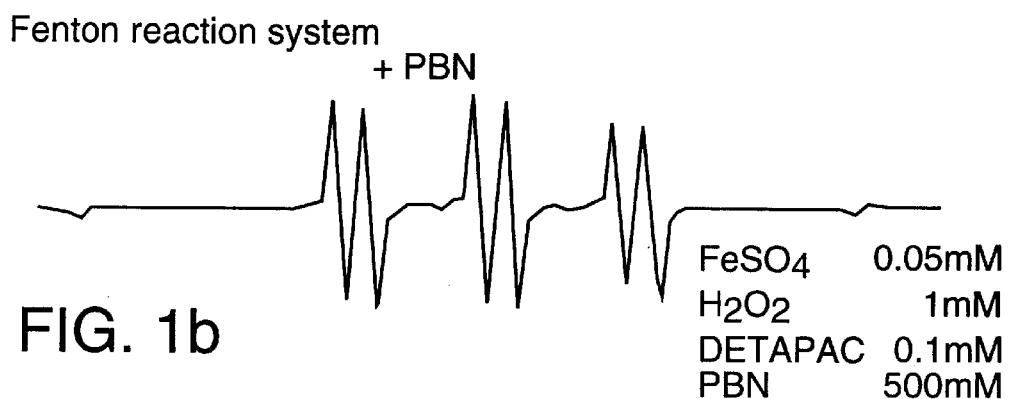
FIG. 1(b) is an ESR spectrum of a Fenton reaction system, obtained using PBN as a spin-trapping agent.
Figure 1C:
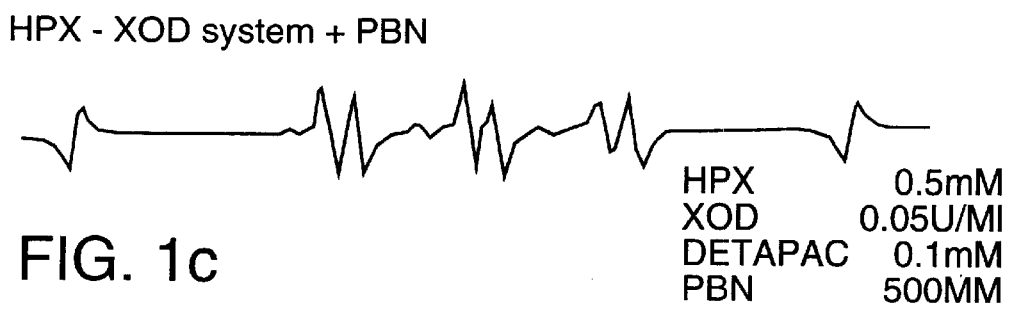
FIG. 1(c) is an ESR spectrum of an HPX-XOD system, obtained using PBN as a spin-trapping agent.
Figure 1D:
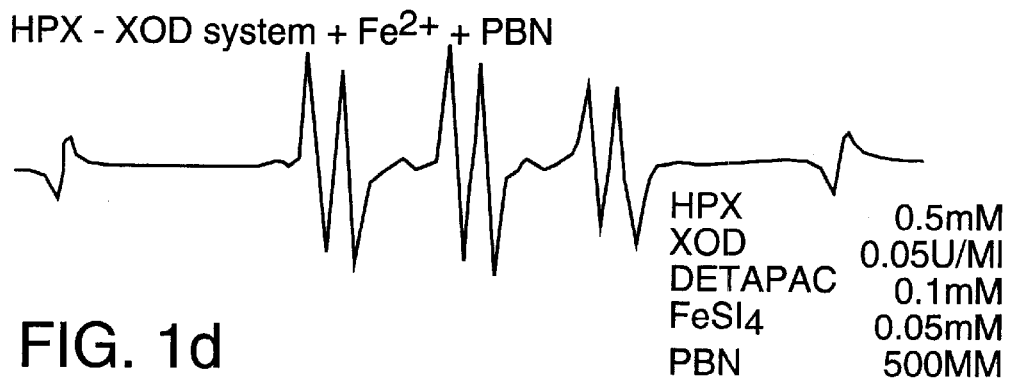
FIG. 1(d) is an ESR spectrum of an HPX-XOD reaction system+$Fe^{2+}$, obtained using PBN as a spin-trapping agent.

FIG. 1(a) shows an ESR spectrum of a human blood plasma. FIG. 1(b) shows an ESR spectrum of a Fenton reaction system. FIG. 1(c) shows an ESR spectrum of an HPXXOD (hypoxanthine-xanthine oxidase) system. FIG. 1(d) is an ESR spectrum of an HPX-XOD reaction system+ $FE^{2+}$. In all of these measurements, PBN was used as a spin-trapping agent.

The Fenton reaction system and the HPX-XOD reaction system+$FE^{2+}$ gave spectra derived from hydroxyl radicals. The HPX-XOD reaction system produced a spectrum derived from superoxide radicals. Comparison of the spacings between the split peaks has revealed that the spectrum of a human blood plasma shown in FIG. 1(a) agrees with the spectra of FIGS. 1(b) and 1(d) derived from hydroxyl radicals. This proves that active oxygen generated in the human blood plasma is hydroxyl radicals.

Figure 2:
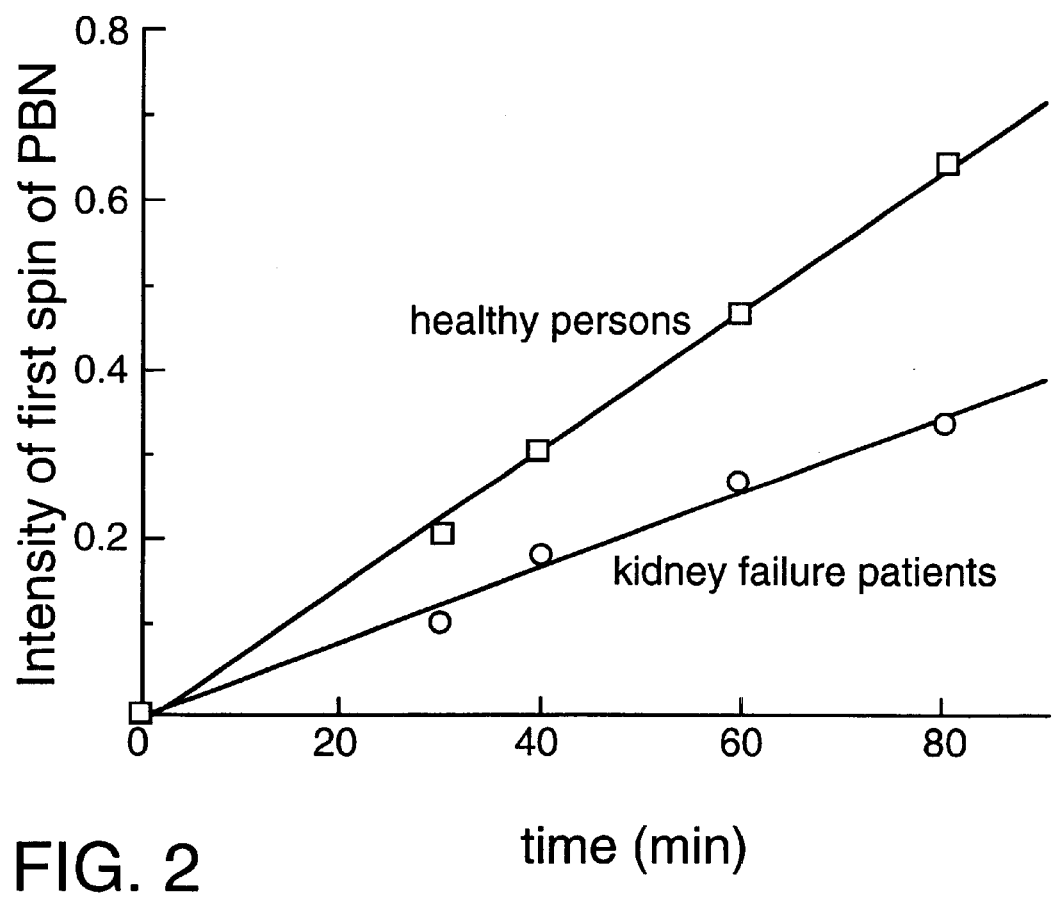
FIG. 2 is a graph in which the intensities of spin adducts derived from healthy persons and from kidney failure patients are plotted against time for which oxidation reactions are performed at 60° C.

FIG. 2 shows the manner in which the amounts of spin adducts derived from kidney failure patients and from healthy persons varied with time. The measurements were performed by ESR spectroscopy. The blood plasmas of the kidney failure patients and of the healthy persons were maintained at 60° C. under the presence of oxygen. It is observed from FIG. 2 that both kinds of plasmas produced hydroxyl radicals at considerable rates immediately after the heating and that the amount of spin adducts increased linearly with the passage of time. A line formed by plotting the amounts derived from the patients has a considerably milder (shallower) gradient than a line obtained by plotting the amounts derived from the healthy persons. Furthermore, when a period of 20 minutes passed, the amount of spin adduct (i.e., the aforementioned ability to generate active oxygen) derived from the patients is smaller than that derived from the healthy persons. Consequently, it can be seen that kidney failure patients can be discriminated from healthy persons by measuring the amounts of spin adducts with the passage of time, finding the gradients of lines obtained by plotting the amounts, and comparing them against appropriately selected threshold values.

EXAMPLE 2

Figure 3:
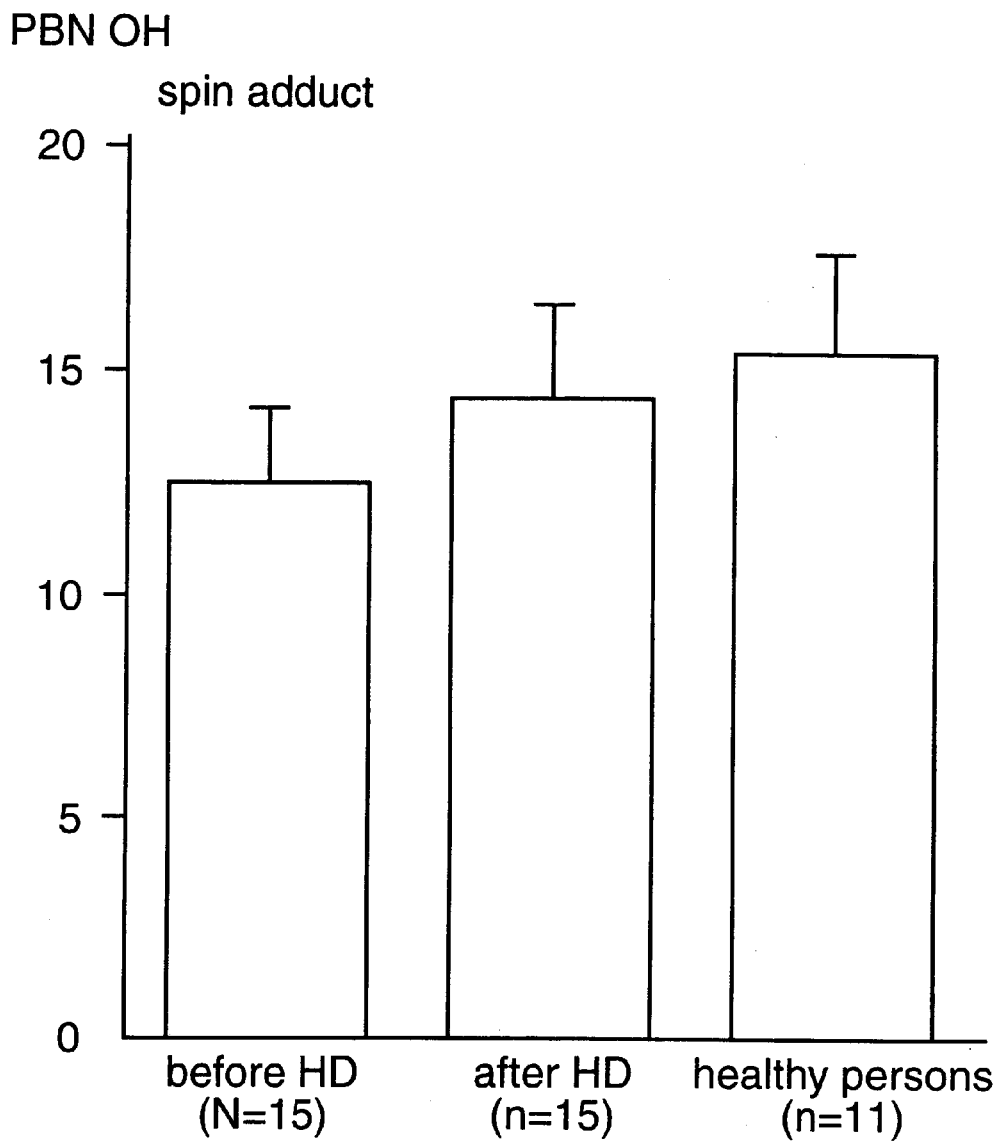
FIG. 3 is a graph representing the intensities of PBN-OH spin adducts derived from blood plasmas of kidney failure patients when an oxidation reaction is performed at 60° C. for 20 minutes, it being noted that some of the patients have been already dialyzed, while the others have not.

FIG. 3 is a graph showing the values of the abilities of three kinds of specimens to generate active oxygen. The values were measured after a lapse of 20 minutes by ESR spectroscopy in the same way as in FIG. 2. The three kinds of specimens are 15 specimens (n=15) (before HD) of kidney failure patients not yet dialyzed, 15 specimens (n=15) (after HD) of kidney failure patients already dialyzed and 11 specimens (n=11) of healthy persons. This graph indicates that the value of the ability of the patients to generate active oxygen made a great difference with that of the healthy persons before the dialysis, but the former value approached that of the healthy persons after the dialysis and was improved.

This result suggests that the ability of blood plasma to generate active oxygen increases or decreases, depending on whether the amount of hydroxyl radicals in the blood plasma that weaken the activity decrease or increase, respectively. It can be understood that a dialysis decreases the active substance that eliminates hydroxyl radicals, thus weakening the ability to eliminate hydroxyl radicals. Conversely, the ability to generate hydroxyl radicals is enhanced. In the human body, active oxygen is effectively utilized. In connection with immunological competence, generation of a certain amount of hydroxyl radicals is essential.

It can be seen from the results of these measurements and discussions that data used to judge whether a dialysis should be ended can be obtained by taking blood from a dialysis patient at appropriate intervals, measuring the value of the ability to generate active oxygen and comparing the resultant values against appropriately set threshold values.

EXAMPLE 3

Figure 4:
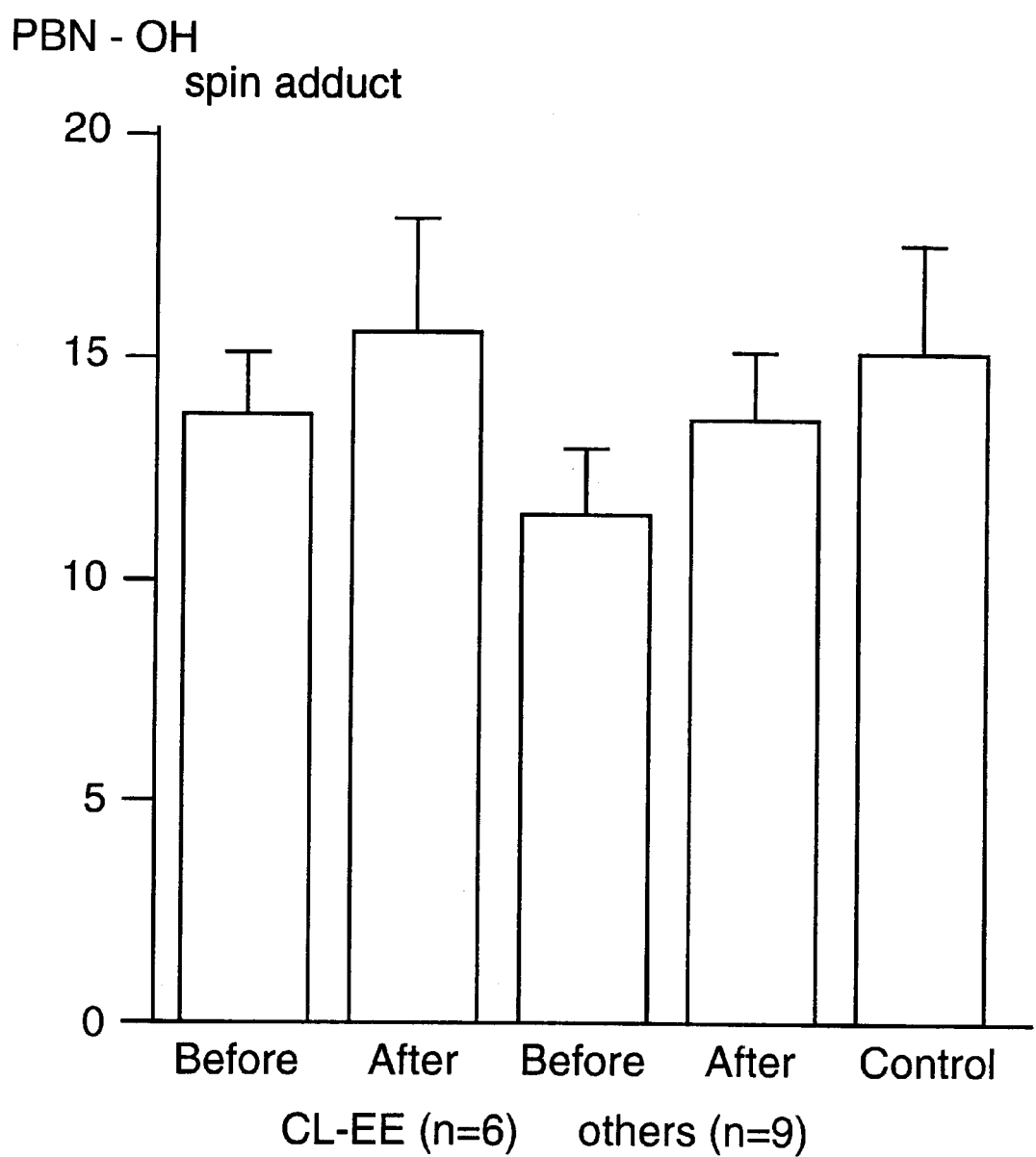
FIG. 4 is a graph representing the intensities of PBN-OH spin adducts derived from blood plasmas of kidney failure patients when an oxidation reaction is performed at 60° C. for 20 minutes, it being noted that the patients have been dialyzed with different dialysis membranes.

Dialysis treatments were made using dialytic materials (CL-EE and others) having different dialytic membranes. The activities of specimens of blood plasma to generate active oxygen were measured. The results are shown in FIG. 4. The right-end bar indicates the value of healthy persons. It is observed that different dialytic membranes give rise to distinctly different measurement results. Hence, such comparisons enable evaluation of dialytic methods and dialytic materials.

As described in detail thus far, in the present invention, the redox of a human blood plasma can be monitored by investigating hydroxyl radicals generated in the blood plasma by ESR spectroscopy. Based on the result, a decision can be made as to whether the person under examination suffers from kidney failure or a diagnosis can be made.

In addition, the present invention makes it possible to make a decision based on the results of measurements as to whether the dialysis treatment can be ended. Furthermore, the dialysis materials can be evaluated. Hence, the burden imposed on the patient can be alleviated. Also, excellent dialysis materials can be developed. In this way, the present invention yields great advantages.

Having thus described our invention with the detail and particularity required by the Patent Laws, what is desired protected by Letters Patent is set forth in the following claims.

What is claimed is:

1. A method of assaying blood from a patient, comprising the steps of:

placing a quantity of blood in the presence of oxygen and heating the blood to a temperature sufficient to generate hydroxyl radicals at a distinguishable rate of increase between healthy blood and diseased blood;

trapping directly at least a portion of the hydroxyl radicals thus generated with a spin-trapping agent to produce a stable spin adduct; and measuring the amount of said spin adduct using an electron spin resonance spectrometer to create ESR signals, and using said ESR signals as the basis of differentiating healthy blood from diseased blood, whereby an ESR signal of hydroxyl radical generation in healthy blood increases at a faster rate than an ESP signal of hydroxyl radical generation in diseased blood.

2. The method of claim 1, wherein said steps of placing said blood in the presence of oxygen and the heating of said blood is effected while maintaining said blood at a given temperature.

3. The method of claim 1, further comprising the step of measuring the amount of the spin adduct derived from the generated hydroxyl radicals with the passage of time, plotting the measured amount of the spin adduct to form a line, finding the gradient of the line and making a judgment based on the degree of the gradient.

4. The method of claim 1, further comprising the step of finding the amount of the spin adduct derived from the generated hydroxyl radicals after a lapse of a given time since beginning of the measurement, and making a judgment based on the found value.

5. A method of judging progress of a dialysis, comprising the steps of:

placing a quantity of blood of a dialysis patient in the presence of oxygen and heating the blood to a temperature sufficient to generate hydroxyl radicals at a distinguishable rate of increase between healthy blood and diseased blood;

trapping directly at least a portion of the hydroxyl radicals thus generated by a spin-trapping agent to produce a stable spin adduct; and measuring the amount of said spin adduct using an electron spin resonance spectrometer to create ESR signals, and using said ESR signals as the basis of differentiating healthy blood from diseased bloods whereby an ESR signal of hydroxyl radical generation in healthy blood increases at a faster rate than an ESR signal of hydroxyl radical generation in diseased blood.

6. The method of claim 5, wherein said steps of placing said blood in the presence of oxygen and the heating of said blood is effected while maintaining said blood at a given temperature.

7. The method of claim 5, further comprising the step of measuring the amount of the spin adduct derived from the generated hydroxyl radicals with the passage of time, plotting the measured amount of the spin adduct to form a line, finding the gradient of the line and making a judgment based on the degree of the gradient.

8. The method of claim 5, further comprising the step of finding the amount of the spin adduct derived from the generated hydroxyl radicals after a lapse of a given time since beginning of the measurement, and making a judgment based on the found value.

* * * * *

UNITED STATES PATENT AND TRADEMARK OFFICE
CERTIFICATE OF CORRECTION

PATENT NO.     : 6,531,320 B1
DATED          : March 11, 2003
INVENTOR(S)    : Masahiro Kohno et al.

It is certified that error appears in the above-identified patent and that said Letters Patent is hereby corrected as shown below:

<u>Title page,</u>
Item [73], insert
-- [73] Assignee: Jeol Ltd. (JP) --.

Signed and Sealed this

Sixteenth Day of December, 2003

JAMES E. ROGAN
*Director of the United States Patent and Trademark Office*